United States Patent
Redmond et al.

(10) Patent No.: US 7,345,039 B2
(45) Date of Patent: *Mar. 18, 2008

(54) ENHANCEMENT OF EFFECTIVENESS OF 5-FLUOROURACIL IN TREATMENT OF TUMOR METASTASES AND CANCER

(75) Inventors: H. Paul Redmond, Cork (IE); Rolf W. Pfirrmann, Lucerne (CH)

(73) Assignee: Ed. Geistlich Soehne AG fuer chemische Industrie, Wolhusen (CH)

(*) Notice: Subject to any disclaimer, the term of this patent is extended or adjusted under 35 U.S.C. 154(b) by 340 days.

This patent is subject to a terminal disclaimer.

(21) Appl. No.: 10/660,798

(22) Filed: Sep. 12, 2003

(65) Prior Publication Data

US 2004/0087579 A1    May 6, 2004

Related U.S. Application Data

(60) Continuation-in-part of application No. 10/281,138, filed on Oct. 28, 2002, now Pat. No. 6,815,441, which is a division of application No. 09/583,902, filed on Jun. 1, 2000, now Pat. No. 6,479,481, application No. 10/660,798, which is a continuation-in-part of application No. 09/993,896, filed on Nov. 27, 2001, now abandoned.

(60) Provisional application No. 60/253,138, filed on Nov. 28, 2000, provisional application No. 60/182,200, filed on Feb. 14, 2000, provisional application No. 60/174,607, filed on Jan. 5, 2000, provisional application No. 60/167,681, filed on Nov. 29, 1999, provisional application No. 60/151,050, filed on Aug. 27, 1999, provisional application No. 60/137,421, filed on Jun. 4, 1999.

(51) Int. Cl.
*A61K 31/54* (2006.01)
*A61K 31/505* (2006.01)

(52) U.S. Cl. .................................. 514/223.8; 514/274

(58) Field of Classification Search .............. 514/223.5
See application file for complete search history.

(56) References Cited

U.S. PATENT DOCUMENTS 6,303,596 B1 * 10/2001 Morrissey et al. ....... 514/222.5
6,479,481 B1    11/2002 Stendel et al.

FOREIGN PATENT DOCUMENTS

EP    1 066 830 A2    1/2001
WO    WO 92/00743 A1   1/1992

OTHER PUBLICATIONS

Braumann, C., et al., "The Influence of Intraoperative Intravenous and Intraperitoneal Application of Taurolidine with Heparin on Subcutaneous and Intraperitoneal Tumor Growth in Laparoscopic Surgery in a Rat Model", *Department of Surgery, Humboldt-University of Berlin, Campus Chartié Mitte, Schumannstr. 20-21*, 10098 Berlin, Germany, Apr. 14th and 15th, 2000, 3 pages.
Carter, S., et al., "Chemotherapy of Cancer", Second Edition, A Wiley Medical Publication, pp. 77-78.
Foye, W., "Cancer Chemotherapeutic Agents", *American Chemical Society*, Washington, DC, 1995, pp. 50-55.
Jacobi, C.A., et al., "Intraperitoneal Instillation of Taurolidine and Heparin for the Prevention of intraperitoneal Tumor Growth and Trocar Metastases in Laparoscopic Surgery in a Rat Model", *Langebecks Arch Chir*, (1997) 382 Suppl. 1: S31-S36.
Jacobi, C.A., et al., "Influence of Different Gases and Intraperitoneal Instillation of Antiadherent or Cytotoxic Agents on Peritoneal Tumor Cell Growth and Implantation with Laparoscopic Surgery in a Rat Model", *Surg Endosc*, (1999) 13:1021-1025.
Jacobi, C.A., et al., "New Therapeutic Strategies to Avoid Intra-and Extraperitoneal Metastases during Laparoscopy: Results of a Tumor Model in the Rat", *Dig Surg*, 1999; 16:393-399.
Jacobi, C.A., et al., "Inhibition of Peritoneal Tumor Cell Growth and Implantation in Laparoscopic Surgery in a Rat Model", *The American Journal of Surgery*, (1997) vol. 174, pp. 359-363.
Hansen, L., et al., "Altretamine", *DICP, The Annals of Pharmacotherapy*, 1991, vol. 25, 146-152.
Parfitt, K., "Martindale, the complete drug reference, 32nd ed", (formerly Martindale the extra pharmacopoeia), London: Pharmaceutical press, GB, 534-537.

\* cited by examiner

*Primary Examiner*—Ardin H. Marschel
*Assistant Examiner*—James D. Anderson
(74) *Attorney, Agent, or Firm*—Rothwell, Figg, Ernst & Manbeck P.C.

(57) ABSTRACT

Tumor growth and metastases in cancer patients are inhibited by administration of a combination therapy including effective amounts of 5-Fluorouracil and a methylol transfer agent such as taurolidine, taurultam or mixtures thereof.

3 Claims, No Drawings

ENHANCEMENT OF EFFECTIVENESS OF 5-FLUOROURACIL IN TREATMENT OF TUMOR METASTASES AND CANCER

CROSS-REFERENCE TO RELATED APPLICATION

The present application is a continuation-in-part of U.S. application Ser. No. 09/993,896, filed Nov. 27, 2001 now abandoned, which claims the benefit of U.S. Provisional Application No. 60/253,138, filed Nov. 28, 2000, and the present application also is a continuation-in-part of U.S. application Ser. No. 10/281,138, filed Oct. 28, 2002, U.S. Pat. No. 6,815,441 which is a divisional of U.S. application Ser. No. 09/583,902, filed Jun. 1, 2000, now U.S. Pat. No. 6,479,481 B1, which claims the benefit of U.S. Provisional Application No. 60/137,421, filed Jun. 4, 1999, and which claims the benefit of U.S. Provisional Application No. 60/151,050, filed Aug. 27, 1999, and which claims the benefit of U.S. Provisional Application No. 60/167,681, filed Nov. 29, 1999, and which claims the benefit of U.S. Provisional Application No. 60/174,607, filed Jan. 5, 2000, and which claims the benefit of U.S. Provisional Application No. 60/182,200, filed Feb. 14, 2000.

BACKGROUND OF THE INVENTION

1. Field of the Invention

The present invention relates to the field of treating tumor metastases and cancer.

2. Description of the Background Art

5-Fluorouracil (5-FU) is an antineoplastic drug with clinical activity in a variety of tumors, such as cancers of the colon and rectum, head and neck, liver, breast, and pancreas. One problem with 5-Fu is its extreme toxicity. Since 5-FU targets rapidly dividing cells, the primary toxic side effects are on bone marrow, intestinal mucousa and oral mucousa. Thus, leukocyte and platelet count decreases substantially after administration. Other side effects include stomatitis, diarrhea, nausea and vomiting. Neurological side effects include somnolence and ataxia. Other side effects include chest pain, myocardial necrosis and ischemia. Inflammatory reactions such as acute and chronic conjunctivitis leading to tear duct stenosis and ectropion also occur.

Monotherapy with 5-FU only results in tumor remission in about 20-25% of patients, and the average remission time is only about 6-8 months.

Although combination chemotherapy with 5-FU and other antineoplastic agents has been proposed, typically no substantive additional benefit is provided by the other antineoplastic agents over treatment with 5-FU alone.

Thus, there remains a significant need in the art for new and improved cancer treatment therapies.

SUMMARY OF THE INVENTION

In accordance with the present invention, tumor growth and metastasis is inhibited in a cancer patient by administering to said patient a combination therapy comprising effective amounts of 5-FU and a methylol transfer agent.

DETAILED DESCRIPTION OF THE INVENTION

It has surprisingly been found that methylol transfer agents such as taurolidine and taurultam substantially enhance or augment the antineoplastic effects of 5-FU in a combination therapy for inhibiting tumor metastases and treating cancer in patients. Such methylol transfer agents also substantially reduce the toxic side effects of 5-FU.

5-FU when used in accordance with the present invention includes biologically active derivatives or substantial equivalents thereof.

Methylol transfer agents include methylol-containing compounds such as taurolidine and taurultam. The compounds taurolidine and taurultam are disclosed in U.S. Pat. No. 5,210,083. Other suitable methylol-containing compounds may be found among those identified in PCT Publication No. WO 01/39763. Particularly preferred methylol transfer agents for utilization in accordance with the present invention are taurolidine, taurultam, biologically active derivatives thereof and mixtures thereof.

Particularly preferred embodiments involve treatment of cancers selected from the group consisting of colon cancer, rectal cancer and colo-rectal cancer, as well as inhibition of tumor metastases thereof.

Other cancers to which the combination therapy of the present invention is effective may include other carcinomas, sarcomas or lymphomas, cancers of the head and neck, liver cancer, breast cancer and pancreatic cancer. Cancers to which the present invention may be applicable include glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, melanoma, renal cell cancer and metastases thereof.

Effective daily dosage amounts of 5-FU may be in the range of about 0.1-1,000 mg per pharmaceutical dosage unit. Effective dosage amounts of 5-FU also may be in the range of about 100-5,000 mg/m$^2$ body surface area, preferably about 200-1,000 mg/m$^2$ body surface area, more preferably about 500-600 mg/m$^2$ body surface area. 5-FU typically is provided in 250 mg or 500 mg ampules for injection, or 250 mg capsules for oral administration.

Effective dosage amounts of a methylol transfer agent in accordance with the present invention may comprise pharmaceutical dosage units within the range of about 0.1-1,000 mg/kg. Preferred dosages may be in the range of about 10-20 grams taurolidine, taurultam or a mixture thereof, per administration.

Pharmaceutical dosage units of the combined therapy of the present invention may be administered by any suitable route, which include oral, topical or peritoneal administration, e.g., subcutaneously, intraperitoneally, intramuscularly, or intravenously, e.g., by infusion or injection.

In preferred embodiments, 250 ml of taurolidine 2% solution is administered by intravenous infusion about 1-6 times per day, more preferably about 2-4 times per day, during a treatment period, concurrently or sequentially with administration of 5-FU at a preferred dosage within the range of about 500-600 mg/m$^2$ body surface area. In accordance with one embodiment, 5-FU is administered by bolus intravenous injection at a dosage of 500 mg/m$^2$ body surface area, 1-3 days per week for a total of three weeks, during a treatment period including administration of taurolidine and/or taurultam. In an alternative embodiment, a 600 mg/m$^2$ intravenous bolus injection is administered 1-2 times per week during a three week treatment period, along with administration of taurolidine and/or taurultam as indicated above.

The present invention also is directed to a combination of 5-FU and a methylol transfer agent, in effective amounts for simultaneous, separate or sequential use for inhibiting tumor metastasis in a cancer patient. The invention also is directed to pharmaceutical combinations including pharmaceutical dosage units comprising effective amounts of 5-Fluorouracil and a methylol transfer agent for inhibiting tumor metastasis in a cancer patient, as well as to pharmaceutical compositions comprising such combinations.

In contrast with other antineoplastic agents, methylol transfer agents such as taurolidine and taurultam surprisingly and substantially enhance or augment the antineoplastic effects of 5-FU, and substantially reduce the extreme toxic side effects of 5-FU. Accordingly, with a combination therapy of 5-FU and a methylol transfer agent such as taurolidine and/or taurultam, the amount of 5-FU can be reduced to achieve the same activity as larger dosages of 5-FU alone, while encountering fewer toxic side effects. Alternatively, combination therapy in accordance with the present invention can be utilized with the same 5-FU dosage levels as monotherapy with 5-FU, while achieving enhanced antineoplastic results along with fewer side effects.

The invention is further illustrated by the following non-limiting example.

EXAMPLE 1

The human colo-rectal cell lines SW 480 (primary), SW 620 (metastatic) and W 707 (metastatic) were incubated with the following: culture medium (control), taurolidine at 5, 10, 25, 50 and 100 µg/ml doses, and 5-Fluorouracil (5-FU) at 5, 10, 25, 50 and 100 µM doses. 5-FU was tested alone, and together with taurolidine. Cell proliferation, apoptosis and cell cycle were assessed.

There was a significant decrease in tumor cell proliferation at 24 hours. There was no significant increase in taurolidine-induced apoptosis and taurolidine did not alter the phases of the cell cycle. There was an increase in LDH release ($p=.0011$), which correlated with inhibited tumor proliferation. Taurolidine was found to augment the effects of given doses of 5-FU ($p=0.0001$).

The invention claimed is:

1. A method of inhibiting colo-rectal tumor growth in a cancer patient comprising administering to said patient a combination therapy comprising effective amounts of 5-Fluorouracil (5-FU) and taurolidine, said taurolidine being capable of substantially enhancing antineoplastic effects of said 5-FU, substantially reducing toxic side effects of said 5-FU, or a combination thereof, wherein said taurolidine has a substantial effect on activity of said 5-FU, said substantial effect being selected from the group consisting of substantially enhancing antineoplastic effects of said 5-FU, substantially reducing toxic side effects of said 5-FU, and a combination thereof.

2. The method of claim 1 wherein said tumor growth is metastatic tumor growth.

3. A combination comprising 5-FU and taurolidine in effective amounts for simultaneous, separate or sequential use for inhibiting tumor growth in a colo-rectal cancer patient, said taurolidine being capable of substantially enhancing antineoplastic effects of said 5-FU, substantially reducing toxic side effects of said 5-FU, or a combination thereof, wherein said taurolidine has a substantial effect on activity of said 5-FU, said substantial effect being selected from the group consisting of substantially enhancing antineoplastic effects of said 5-FU, substantially reducing toxic side effects of said 5-FU, and a combination thereof.

* * * * *